United States Patent [19]

Pfirrmann et al.

[11] 4,226,858

[45] Oct. 7, 1980

[54] METHOD AND COMPOSITION FOR THE TREATMENT OF SCARS

[75] Inventors: Rolf W. Pfirrmann, Lucerne; Otto Wicki, Wolhusen, both of Switzerland

[73] Assignee: Ed. Geistlich Sohne A.G. fur Chemische Industrie, Lucerne, Switzerland

[21] Appl. No.: 43,745

[22] Filed: May 30, 1979

[30] Foreign Application Priority Data

May 31, 1978 [GB] United Kingdom ............... 25601/78

[51] Int. Cl.³ ........................... A01N 9/02; A01N 9/08
[52] U.S. Cl. .................................................... 424/195
[58] Field of Search ........................................ 424/195

[56] References Cited

PUBLICATIONS

J.A.C.S. vol. 82 (1975) Pars. 7652r article by Cotaescu et al.

*Primary Examiner*—Elbert L. Roberts
*Attorney, Agent, or Firm*—Bacon & Thomas

[57] ABSTRACT

The invention provides compositions comprising oleum hyoscyami together with a pharmaceutical carrier or excipient and a method for the prevention or treatment of scar tissue whereby existing scar tissue or a wound or surgical incision is treated topically with oleum hyoscyami.

5 Claims, No Drawings

METHOD AND COMPOSITION FOR THE TREATMENT OF SCARS

DESCRIPTION

This invention relates to a method and composition for the treatment of scars.

Hypertrophic scars and keloids are an almost inevitable result of injury and surgery and hitherto there has been no available method for their prevention or removal. A number of techniques have been proposed for the elimination of scars, such as treatments with hydrocortisone, collagen, vitamins such as Vitamins E and A, and extracts from animal organs such as placenta, but no reliably effective composition or method has been discovered.

We have now found that the active components of oleum hyoscyami are surprisingly effective in the prevention and elimination of scars. This oil has been known from ancient times for the alleviation of tooth and ear pains; the oil has always hitherto been used as such, however, and has never been associated in any with the treatment of wounds or scars.

We have now found that regular application of oleum hyoscyami either to a healing wound or surgical incision or to an existing scar is remarkably effective in preventing or removing the formation of disfiguring scar tissue.

The active components of oleum hyoscyami are parasympathetic-blocking alkaloids such as atropine, scopolamine and hyoscyamine, as well as copper phyllocyanates. It appears that all these components exert a surprisingly beneficial action upon the scar tissue.

According to the present invention, therefore, we provide a method for the prevention or elimination of scars whereby a wound or surgical incision or an existing scar is treated with a parasympathetic-blocking alkaloid such as atropine, scopolamine or hyoscyamine, and/or a copper phyllocyanate. In general, the above active substances will be used in combination in the form of oleum hyoscyamine.

The above active substances may be applied to the affected area prophylactically or post-operatively for a period of 2-3 weeks after the injury or surgical treatment. In this way it is normally possible to avoid formation of disfiguring scars, contractures or keloids. The active material can also be applied to hypertropic keloid-forming scar tissues after surgical operations, for example skin transplants, and also in the case of burns and wounds. Even where a second corrective operation is required, the treatment according to the invention can provide advantageous pre-treatment. In general, the redness of fresh scar tissues is more rapidly returned to the normal skin colour.

In general, oleum hyoscyami comprises the active components in a vegetable oil such as arachis oil. According to the Pharmacopoeia Helvetia, VI, page 391, the oil is formed by moistening leaves of hyoscyamus (100 g) and copper powder R (3 g) with 94% aqueous ethanol (100 g) and 10% aqueous ammonia (50 g) and allowed to stand for 24 hours in a covered container. The mixture is then heated on a water bath with vigorous stirring with arachis oil pre-heated to 60°-70° C. until the smell of ammonia has disappeared and the oil has clarified. After removal of the solids and pressing, the liquid is filtered. The preparation contains about 0.005% alkaloids as bases and copper phyllocyanate formed by reaction of the copper with extracted chlorophyll.

According to the invention, the active components of the oleum hyoscyami are preferably formulated in compositions together with pharmaceutical carriers and/or excipients.

The formulations should be suitable for topical application by rubbing on to the scar tissue and may thus comprise creams, emulsions, lotions, oils, gels and aerosols.

Creams and emulsions may comprise water-in-oil emulsions which are readily applied to the skin and lead to good absorption of the active components. The compositions may advantageously contain oil-soluble vitamins A and E as well as water-soluble vitamins, which are particularly favourable for skin treatment, such as vitamins of the B complex. Amino acid-containing complexes are also of use, for example collagen, which regulates the water-uptake of the skin.

Oil-in-water emulsions are also possible for the formulation of creams and lotions.

In general emulsions will contain appropriate surfactants which are preferably non-ionic. Suitable surfactants include glyceryl esters of long-chain fatty acids such as triglyceryl diisostearate, conveniently in a mixture with long-chain fatty acid ethanolamides such as isostearic acid diethanolamide, or glyceryl monostearate; alkoxylated long-chain alcohols such as ethoxylated or propoxylated lanolin alcohol; alkoxylated fatty acid esters, e.g. ethoxylated esters; sugar alcohol esters of long-chain fatty acids such as sorbitan sesquioleate. Oils and waxes may conveniently be present, such as white paraffin wax or bleached beeswax, microcrystalline wax, paraffin oil and synthetic waxes such as polyethylenes. A preservative will commonly be present.

Oily preparations may contain oils in addition to the arachis oil in the oleum hyoscyami, for example esters of long chain fatty acids such as isopropyl palmitate, isoadipate or myristate or ethylhexyl palmitate.

Gels according to the invention may comprise thickening agents based on silica, for example Aerosil 200 (Degussa).

Aerosol formulations may, for example, take the form of aerosol foams which may contain, for example, about 50% oleum hyscyami. Suitable propellants include propane/butane, isobutane, carbon dioxide and fluorinated hydrocarbons. Aerosols have the advantage of easy application, sterile packaging and convenient in carrying.

In all of the above formulations, the content of oleum hyoscyami will range between 10% and 60%. A preferred level is about 50%.

In general, the semi-solid formulations such as creams, emulsions, gels and aerosol foams are preferred to the liquid oils.

The hyoscyamus leaves used as starting material in the preparation of the oil are described in detail in European Pharmacopoeia, Volume 1, page 289.

The following examples are given by way of illustration only:

EXAMPLE 1

| | |
|---|---:|
| Non-ionic water-in-oil emulsifying agent* | 3,00% |
| Hydroxylated lanolin | 2,20% |
| Cera alba | 15,00% |
| Methyl p-hydroxybenzoate | 0,20% |

-continued

| | |
|---|---|
| Oleum hyoscyami (Ph.H.VI) | 50,00% |
| Collagen 15%, (sterile-filtered) | 5,00% |
| Polyethylene-glycol B.P. | 5,00% |
| Perfume oil | 0,70% |
| Demineralised water, sterile-filtered | ad. 100,00% |

EXAMPLE 2

| | |
|---|---|
| Hydroxylated lanolin | 2,20% |
| Oleum hyoscyami | 50,00% |
| Non-ionic water-in-oil emulsifying agent* | 3,00% |
| Beeswax, bleached | 15,00% |
| p-Hydroxybenzoic acid methyl ester | 0,20% |
| p-Hydroxybenzoic acid propyl ester | 0,02% |
| Polyethylene-glycol B.P. | 5,00% |
| Perfume oil | 0,50% |
| Demineralised water, sterile-filtered | ad. 100,00% |

*Mixture of triglyceryl diisostearate and isostearoyl diethanolamide.

The above components are formed into a water-in-oil emulsion by conventional techniques.

EXAMPLE 3

| | |
|---|---|
| Hydroxylated lanolin | 3,00% |
| Oleum hyoscyami | 50,00% |
| Beeswax, bleached | 10,00% |
| Propyl ester of lanolin alcohol | 2,00% |
| Glyceryl-monostearate | 2,00% |
| Micro-wax | 5,00% |
| Borax | 0,60% |
| p-Hydroxybenzoic acid methyl ester | 0,20% |
| p-Hydroxibenzoic acid propyl ester | 0,02% |
| Propylene-glycol | 5,00% |
| Perfume oil | 0,50% |
| Demineralised water, sterile-filtered | ad. 100,00% |

The above components are formed into a water-in-oil emulsion by conventional techniques.

EXAMPLE 4

| | |
|---|---|
| Microwax | 24,00% |
| Paraffin wax (hard) | 20,50% |
| Propoxylated lanolin alcohol with 5 Mol. Propylene-oxide | 2,00% |
| Lanolin alcohol absorption base | 0,30% |
| Oleum hyoscyami | 50,00% |
| Perfume oil | 0,50% |
| p-Hydroxybenzoic acid methyl ester | 0,15% |
| p-Hydroxybenzoic acid propyl ester | 0,02% |
| Demineralised water, sterile-filtered | ad. 100,00% |

The above components are formed into a water-in-oil emulsion by conventional techniques.

EXAMPLE 5

| | |
|---|---|
| Oleum hyoscyami | 50,00% |
| Sorbitan sesquioleate | 3,00% |
| AC-Polyethylene | 10,00% |
| Hydroxylated lanolin | 2,00% |
| Cis-1-1-(3 chloroallyl)-3,5,7-triaza-1-azoniaadamantane chloride | 0,10% |
| Sorbitol | 5,00% |
| Perfume oil | 0,50% |
| Demineralised water, sterile-filtered | ad. 100,00% |

The above components are formed into a water-in-oil emulsion by conventional techniques.

EXAMPLE 6

| | |
|---|---|
| Oleum hyoscyami | 16,00% |
| Stearic acid | 8,00% |
| Cetyl alcohol | 1,00% |
| Polyoxyethylene fatty acid ester | 5,00% |
| Propylen glycol | 3,50% |
| Cis-1-1-(3 chloroallyl)-3,5,7-triaza-1-azoniaadamantane chloride | 0,20% |
| Perfume oil | 0,20% |
| Demineralised water, sterile-filtered | ad. 100,00% |

The above components are formed into a water-in-oil emulsion by conventional techniques.

EXAMPLE 7

| | |
|---|---|
| Diethanolamine cetyl-phosphate complex | 3,00% |
| Wool wax alcohol | 5,00% |
| Paraffin oil perl. | 5,00% |
| Glyceryl monostearate non-self emulsifying | 5,00% |
| Oleum hyoscyami | 20,00% |
| p-Hydroxybenzoic acid methyl ester | 0,18% |
| p-Hydroxybenzoic acid propyl ester | 0,02% |
| Sorbitol 70% | 5,00% |
| Perfume oil | 0,20% |
| | ad. 100,00% |

The above components are formed into a water-in-oil emulsion by conventional techniques.

EXAMPLE 8

| | |
|---|---|
| Beeswax | 7,00% |
| Absorption base Amerchol 500 | 3,00% |
| Lanolin alcohol ethoxilate with 16 Mol. ethylene-oxide | 2,00% |
| Glycerylmonostearate, non-self emulsifying | 2,00% |
| Microwax | 5,00% |
| Oleum hyoscyami | 30,00% |
| Petroleum jelly | 4,00% |
| 2-Ethylhexyl palmitate | 10,00% |
| Sorbitol | 5,00% |
| Cis-1-1-(3 chloroallyl)-3,5,7-triaza-1-azoniaadamantane chloride | 0,20% |
| Perfume oil | 0,20% |
| Demineralised water, sterile-filtered | ad. 100,00% |

The components are formed into an oil-in-water emulsion using conventional techniques.

EXAMPLE 9

Oil

| | |
|---|---|
| Oleum hyoscyami | 50,00% |
| Isopropyl palmitate | 30,00% |
| Isopropyl isoadipate | 20,00% |

EXAMPLE 10

Oil

| | |
|---|---|
| Oleum hyoscyami | 50,00% |
| 2-ethylhexyl palmitate | 30,00% |
| Isopropyl isoadipate | 19,00% |
| Perfume oil | 0,50% |

EXAMPLE 11

Gel

| | |
|---|---|
| Oleum hyoscyami | 50,00% |
| Paraffin oil | 20,00% |
| Aerosil 200 | 8,00% |
| Isopropyl myristate | 12,00% |
| 2-ethylhexyl palmitate | 10,00% |

The components are formed into a gel by conventional techniques.

What we claim is:

1. Method for the prevention or removal of scar tissue whereby existing scar tissue or a wound or surgical incision is treated topically with oleum hyoscyami.

2. Method as claimed in claim 1 in which the scar tissue or potential scar tissue treated results from a skin graft, a burn, a wound or a surgical incision.

3. Topical pharmaceutical compositions for the prevention or removal of scar tissue, comprising an effective amount of oleum hyoscyami together with a pharmaceutical carrier or excipient.

4. Compositions as claimed in claim 3 in the form of creams, emulsions, gels or aerosols.

5. Compositions as claimed in claim 3 or claim 4 containing 10–60% by weight of oleum hyoscyami.

* * * * *